United States Patent
Wang et al.

(10) Patent No.: US 9,335,307 B2
(45) Date of Patent: May 10, 2016

(54) GAS CHROMATOGRAPH

(71) Applicants: Aosheng Wang, Eden Prairies, MN (US); Ray Dean Shepherd, Tulsa, OK (US); Christoph Klawun, Bartlesville, OK (US)

(72) Inventors: Aosheng Wang, Eden Prairies, MN (US); Ray Dean Shepherd, Tulsa, OK (US); Christoph Klawun, Bartlesville, OK (US)

(73) Assignee: Siemens Aktiengesellschaft, Munich (DE)

( * ) Notice: Subject to any disclaimer, the term of this patent is extended or adjusted under 35 U.S.C. 154(b) by 314 days.

(21) Appl. No.: 14/018,185

(22) Filed: Sep. 4, 2013

(65) Prior Publication Data

US 2014/0076023 A1 Mar. 20, 2014

Related U.S. Application Data

(60) Provisional application No. 61/697,085, filed on Sep. 5, 2012.

(30) Foreign Application Priority Data

Sep. 5, 2012 (EP) .................................... 12183059

(51) Int. Cl.
*G01N 7/00* (2006.01)
*G01N 30/66* (2006.01)
*G01N 30/86* (2006.01)

(52) U.S. Cl.
CPC ................ *G01N 30/66* (2013.01); *G01N 30/86* (2013.01)

(58) Field of Classification Search
CPC ... G01N 30/02; G01N 30/00; G01N 30/6095; G01N 30/74; A61K 2300/00; C07C 5/48; C07C 67/333; C07C 11/02; C01B 2203/0244; C01B 2203/1023
USPC .......... 73/23.4, 23.22, 23.35, 61.52, 862.472, 73/23.39
See application file for complete search history.

(56) References Cited

U.S. PATENT DOCUMENTS 4,164,862 A    8/1979   Jackson
4,741,198 A    5/1988   Farren et al.
4,891,120 A *  1/1990   Sethi ................. G01N 30/6086
                                                        204/600

(Continued)

FOREIGN PATENT DOCUMENTS

| CN | 102183605 | 9/2011 |
|---|---|---|
| DE | 19624683 | 10/1997 |
| JP | 91-78721 | 7/1997 |
| WO | WO 03/083467 | 10/2003 |

*Primary Examiner* — Peter Macchiarolo
*Assistant Examiner* — Mohammed E Keramet-Amircolai
(74) *Attorney, Agent, or Firm* — Cozen O'Connor

(57) ABSTRACT

A gas chromatograph in which components of a sample of a gas mixture are separated via a separation column, a sensing element of a thermal conductivity detector is operated at a first temperature to detect separated components and to generate a detector signal in response to detected components, an evaluation unit evaluates detector signals and determines concentrations of detected components, a further sensing element of a further thermal conductivity detector is operated at a second temperature different from the first temperature, to detect gas components of widely different concentration ranges at high sensitivity, where the thermal conductivity detectors are calibrated for different concentration ranges, and the evaluation unit compares the detector signal with the detector signal of the further thermal conductivity detector to output a concentration value determined from the signal of the thermal conductivity detector calibrated for the measured component concentration.

11 Claims, 2 Drawing Sheets

(56) References Cited

U.S. PATENT DOCUMENTS

| | | | |
|---|---|---|---|
| 6,904,784 B2* | 6/2005 | Allington | B01D 15/12 73/23.35 |
| 7,735,352 B2* | 6/2010 | Alm | G01N 30/463 73/23.4 |
| 2005/0123452 A1* | 6/2005 | Mueller | G01N 30/40 422/89 |
| 2010/0162791 A1* | 7/2010 | Breviere | G01N 1/40 73/23.31 |
| 2012/0024043 A1 | 2/2012 | McBrady et al. | |

\* cited by examiner

GAS CHROMATOGRAPH

CROSS-REFERENCE TO RELATED APPLICATIONS

This is a U.S. non-provisional application and claims priority to U.S. Provisional Application Ser. No. 61/697,085 filed Sep. 5, 2012 and European Application No. 12183059 filed Sep. 5, 2012, the content of which are incorporated herein by reference in their entirety.

BACKGROUND OF THE INVENTION

1. Field of the Invention

The invention relates to a gas chromatograph for analyzing a gas mixture comprising at least one separation column for separating components of a sample of the gas mixture which is fed through the separation column by a carrier gas, a thermal conductivity detector that has a sensing element arranged downstream from the separation column and has a first operating temperature, where the thermal conductivity detector is further configured to detect the separated components in a non-destructive manner and to generate a detector signal in response to each of the detected components, at least one further thermal conductivity detector that has a further sensing element arranged downstream or upstream from the thermal conductivity detector and which is configured to detect separated components and to generate a further detector signal in response to each of the detected components, and an evaluation unit for evaluating the detector signals and further detector signals to determine the concentrations of the detected components.

2. Description of the Related Art

Gas chromatographs are known from WO 03/083467 A2 or US 2005/0123452 A1. Conventional gas chromatographs have several separation columns coupled directly or by a valveless controllable changeover arranged in series. Each separation column is followed by an inline thermal conductivity detector for detecting gas components sufficiently separated up to that point. The thermal conductivity detectors have micro-machined sensing elements comprising micro-machined devices with heated filaments along the axis of a tubular channel. The inner diameters of the channels correspond at least approximately to those of the separation columns so that the sample of the gas mixture is not disturbed at the detector sites. Each sensing element preferably has two inline filaments. These two filaments are diagonally arranged in a Wheatstone bridge together with two filaments of the sensing element of another thermal conductivity detector through which, at the time of the detection, the carrier gas flows.

JP 9 178721 A discloses a gas chromatograph in which a thermal conductivity detector is immediately followed by a flame ionization detector. The thermal conductivity detector is adapted to determine hydrogen and C1 and C2 hydrocarbons, whereas the flame ionization detector is adapted to determine hydrogen and C3 hydrocarbons.

US 2012/0024043 A1 discloses a gas chromatograph with a thermal conductivity detector, another non-destructive detector and a destructive detector coupled in series. The thermal conductivity detector includes sensors for determining properties of the analyte such as a rate of flow, temperature, and/or pressure. The following detectors allow for additional measurement and/or analysis after the thermal conductivity detector determines one or more properties associated with the analyte.

U.S. Pat. No. 4,741,198 A discloses a gas chromatograph where two sensors of a thermal conductivity sensor assembly are disposed in separate cells with one sensor operating at a lower temperature than the other sensor. High concentration samples can be passed through the cell in which the sensor is at the lower temperature while samples with low concentrations of the test gas are passed through the sensor operating at the higher temperature.

Process gas chromatographs (PGCs), as above-mentioned, are often used to monitor a chemical or petrochemical process to ensure the stability of the process and/or the quality of the products from the process. Thermal conductivity detectors are commonly used in PGCs to measure concentrations of gas components eluting from the separation columns. Depending on the nature of a PGC application, many components of widely different concentration ranges can be present in a same analysis cycle and widely different concentration ranges of a same component can occur at different analysis cycles. A higher temperature of the sensing elements of a TCD is often used to improve detector sensitivity for the components of lower concentrations, and a lower temperature is often used to improve detector linear ranges for the components of higher concentrations. However, as only one temperature can be used in a conventional TCD to cover different concentration ranges, a compromised mid-range temperature must often be found, resulting in decreases in both detector sensitivity and linear range and thus sacrificing result accuracy for some components.

SUMMARY OF THE INVENTION

It is therefore an object of the invention to detect gas components of widely different concentration ranges at high sensitivity.

This and other objects and advantages are achieved in accordance with the invention by providing a gas chromatograph that includes at least one further thermal conductivity detector that is arranged immediately downstream or upstream from the thermal conductivity detector to detect the same separated components as the thermal conductivity detector and has a second operating temperature different from said first temperature, where the thermal conductivity detector and the at least one further thermal conductivity detector are calibrated for different concentration ranges, and the evaluation unit is further configured to compare the detector signal for an actually detected component with the further detector signal to determine in which of the different concentration ranges that the concentration of the actually detected component is located and to output a concentration value determined from the signal of the thermal conductivity detector that is calibrated for the concentration of the component measured.

The gas chromatograph in accordance with the invention takes advantage of redundant measurements at different temperatures. To this end, the sensing elements of different thermal conductivity detectors are arranged inline and operated at a different temperature that is selected to optimize either sensitivity or linear range for the concentration ranges expected. The sensing element with the higher operating temperature may be calibrated for components of lower concentrations and the sensing element with the lower operating temperature can be calibrated for components of higher concentrations. Different components of different concentrations are always measured on all sensing elements regardless of concentrations, and data analysis software in the evaluation unit can dynamically select the best result of the measured component concentration from the sensing element of a temperature that is best for the concentration of the component measured. As a result, more accurate results can be obtained at both high and low concentrations in all analysis cycles.

The at least one further detector is preferably identical in configuration to the thermal conductivity detector. The different temperatures of the respective sensing elements may be set by powering the sensing elements with different voltages or currents.

To prevent the different temperatures drifting apart, the sensing element of the thermal conductivity detector and the further sensing element of the at least one further thermal conductivity detector are preferably integrated in a single component or at least thermally coupled on a common substrate.

It is known to use a thermal conductivity detector in series with a flame ionization detector for analyzing complex mixtures where different types of detectors are needed for different gas components to be measured. The information provided by the two techniques is complimentary and not redundant and thus does not serve the purpose of the present invention. This is also true for thermal conductivity detectors with two inline filaments, which are commercially available and have been used in process gas chromatographs as the above-mentioned US 2005/0123452 A1 shows. In contrast to this, in accordance with an embodiment of the invention, micro-machined devices with two inline filaments along the axis of a tubular channel may be preferably used while the two inline filaments belong to different redundant thermal conductivity detectors and are heated to different temperatures.

Although more complex electronics and data analysis software will be required for the gas chromatograph in accordance with the invention, the increased analyzer cost may well be justified by the improved result accuracy. For example, this improved accuracy is important for emission monitoring for compliances with environmental regulations, as well as for product quality control in a process environment.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The invention will now be described in greater detail by way of example and with reference to the drawing figures in which.

DETAILED DESCRIPTION OF THE PREFERRED EMBODIMENTS

Figure 1:
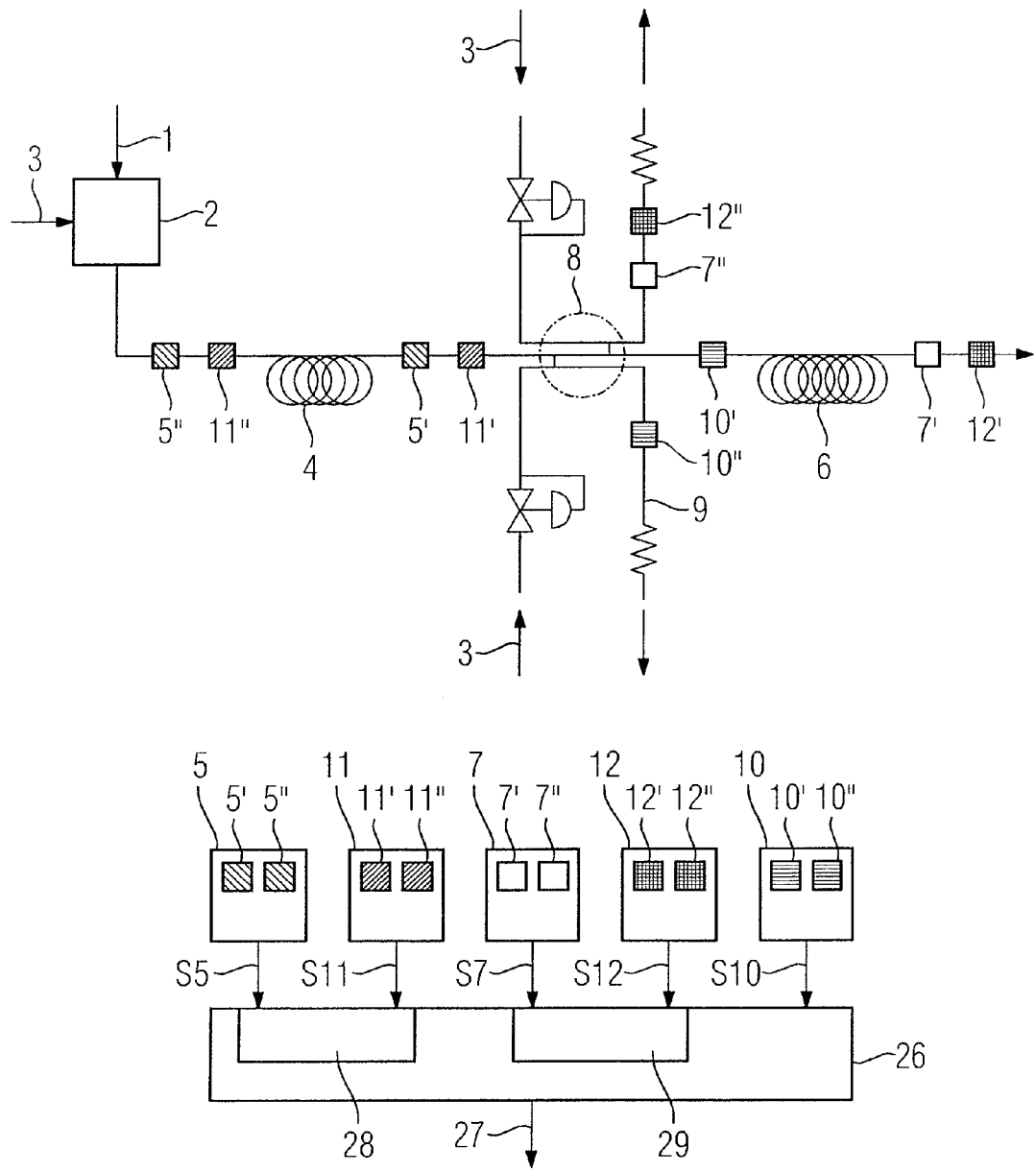
FIG. 1 illustrates an exemplary embodiment of the gas chromatograph in accordance with the invention.

In the following description, like reference numerals designate like parts or elements.

FIG. 1 illustrates a gas chromatograph for analyzing a gas mixture 1. A sample of the gas mixture 1, which has been removed from a technical process and treatment, is supplied to a dosing unit 2. The dosing unit 2 is used to inject a specified dose of the gas sample as a short and sharply delimited dosing plug into a carrier gas stream 3 at a predefined instant. The dose and the carrier gas are supplied to a separation column combination in which the gas components contained in the sample plug are separated and sequentially detected and quantitatively identified.

In the illustrated example, the separation column combination consists of a first separation column 4 followed by a sensing element 5' of a first thermal conductivity detector (TCD) 5, and a second separation column 6 followed by a sensing element 7' of a second TCD 7. The separation columns 4, 6 and the sensing elements 5', 7' are arranged in line in a series connection. A controllable changeover device 8 is arranged between the separation columns 4 and 6, in this case after the sensing element 5' of the first TCD 5.

The first separation column 4 is configured to separate gas components, such as higher hydrocarbons, which have higher retention times and which are detected by the first TCD 5.

The second separation column 6 is configured to separate gas components, such as carbon dioxide or nitrogen, which have lower retention times and which are detected by the second TCD 7.

There may be certain gas components that must be prevented from reaching the second separation column 6 because they cannot or can only be removed by conditioning this separation column 6. For this reason, these unwanted gas components, after they exit from the first separation column 4, are discharged via a gas path 9 via the controllable changeover device 8. The changeover device 8 can be controlled as a function of the presence of the first one of the unwanted gas components at the sensing element 5' of the first TCD 5 or a specified period following the detection of the last one of the gas components admissible for the second separation column 6. A sensing element 10' of an additional TCD 10 is arranged in line between the changeover device 8 and the second separation column 6. This allows for recognizing faults in the adjustment of the changeover device 8 by comparing the measurements of TCDs 5 and 10.

After detection of all interesting gas components to be detected by the first TCD 5, the first separation column 4 is back-flushed with the carrier gas 3 via the controllable changeover device 8, such that all following gas components are removed from the first TCD 5 and the separation column 4.

To provide redundant measurement at different temperatures, the sensing elements 5', 7' of the TCDs 5, 7 are immediately followed by sensing elements 11', 12' of respective redundant TCDs 11, 12.

Each of the sensing elements 5', 7', 10', 11', 12' cooperates with a partner sensing element 5", 7", 10", 11", 12" through which the carrier gas 3 flows either continuously or at least at the time when a gas component is detected by the associated one of the sensing elements 5', 7', 10', 11', 12'.

Figure 2:
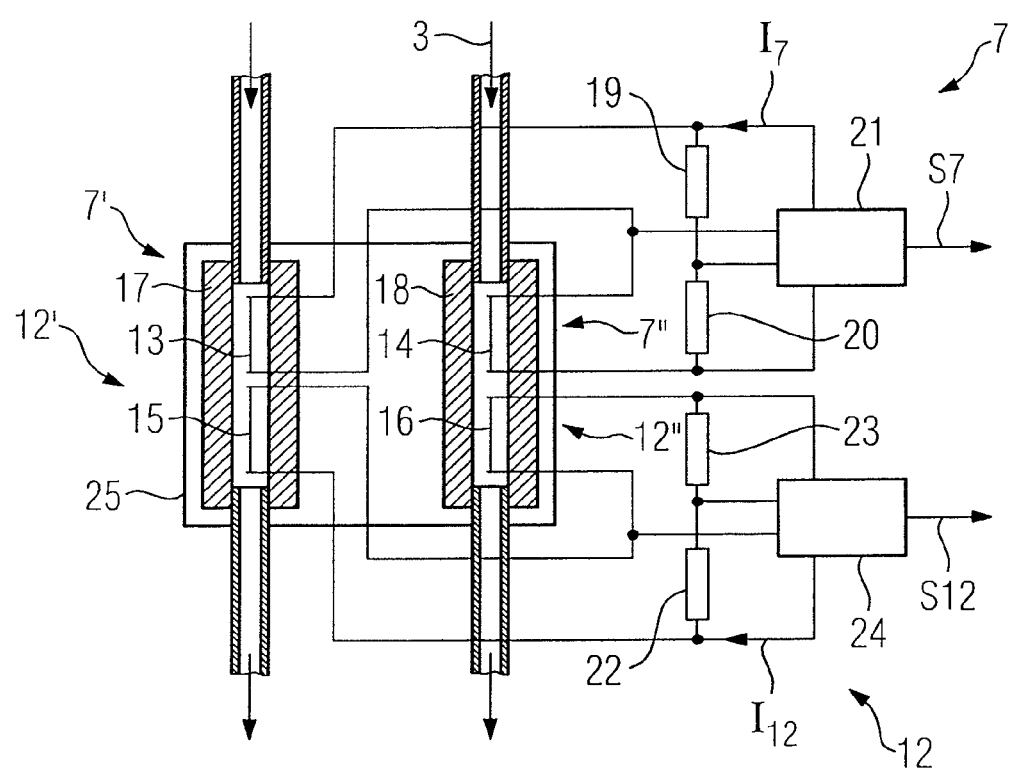
FIG. 2 illustrates an exemplary embodiment of two redundant thermal conductivity detectors.

As FIG. 2 illustrates with the example of TCD 7 and redundant TCD 12, each sensing element 7', 7", 12', 12" has a heated filament 13, 14, 15, 16 which are arranged in pairs 13, 15 and 14, 16 in line in respective tubular channels 17, 18. Channel 17 forms a measurement gas path and channel 18 forms a reference path. The sensing elements 7', 7", or more precisely the filaments 13, 14, of TCD 7 are arranged in a Wheatstone bridge together with fixed resistors 19, 20 of a very low temperature coefficient. The Wheatstone bridge is supplied with a current $I_7$ from a detector circuit 21 at two opposite circuit points, and the voltage that occurs between the two other opposite circuit points is detected by the detector circuit 21 to generate a detector signal S7 of TCD 7. The current $I_7$ is controlled to heat the filaments 13, 14 to a predetermined first temperature when the filaments are completely surrounded by carrier gas 3.

The sensing elements 12', 12", or more precisely the filaments 15, 16, of the redundant TCD 12 are arranged in another Wheatstone bridge together with fixed resistors 22, 23 of a very low temperature coefficient. The Wheatstone bridge is supplied with a current $I_{12}$ from a detector circuit 24 at two opposite circuit points, and the voltage that occurs between the two other opposite circuit points is detected by the detector circuit 24 to generate a detector signal S12 of TCD 12. The current $I_{12}$ is controlled to heat the filaments 15, 16 to a predetermined second temperature that is different from the first temperature of filaments 13, 14.

In the present example, the first temperature is higher than the second temperature and the TCD 7 is calibrated for gas components of lower concentrations whereas the redundant TCD 12 is calibrated for components of higher concentrations.

As illustrated in FIG. 2, the sensing elements 7', 12' in the measurement gas path are preferably integrated in a single component or at least thermally coupled on a common substrate. The component is preferably micro-machined to keep the distance or dead volume between the sensing elements 7', 12' or 7", 12" in the same flow path very small so that peak broadening in chromatograms of subsequent sensing elements can be minimized. The sensing elements 7", 12" in the reference path may be integrated in another component or otherwise thermally coupled. Preferably, all sensing elements 7', 7", 12', 12" of TCDs 7, 12 are attached to a same thermal block 25 for a same constant ambient temperature.

As illustrated in FIG. 1, the other TCDs 5, 10, 11 generate corresponding detector signals S5, S10, S11. The detector signals S5, S7, S10, S11, S12 are provided to an evaluation unit 26 for determining and outputting the concentration values 27 of the detected gas components. The evaluation unit 26 further includes comparing units 28, 29 for comparing the detector signals S5, S7 with the respective redundant detector signals S11, S12 to recognize whether the concentration of the actually measured gas component is in a lower or higher value range. The evaluation unit 26 then outputs the concentration value determined from the signal of the TCD that is calibrated for the concentration of the component actually measured.

The present invention may be embodied in other specific forms without departing from its spirit or essential characteristics. The described embodiments are to be considered in all respects only as illustrative and not restrictive. For example, the Wheatstone bridges shown in FIG. 2 are just classical constructions and there are several different approaches to construct a TCD bridge and several different methods to power and to operate one or more sensing elements in the bridge. In the embodiment of FIG. 1, TCD 10 has no redundant counterpart. However, it may be desirable and is within the scope of the present invention to provide for each TCD a redundant counterpart, regardless of whether it is used for detecting gas components, flow measurement or other purposes.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements which perform substantially the same function in substantially the same way to achieve the same results are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A gas chromatograph for analyzing a gas mixture comprising:
    at least one separation column for separating components of a sample of the gas mixture which is fed through the at least one separation column by a carrier gas;
    a thermal conductivity detector having a sensing element positioned in a flow path downstream from the separation column and arranged in a Wheatstone bridge, the thermal conductivity detector being configured to operate the sensing element at a first operating temperature and to detect the separated components in a non-destructive manner and to generate a detector signal in response to each of the detected components;
    at least one further thermal conductivity detector having a further sensing element positioned in the flow path immediately downstream or upstream from the sensing element of the thermal conductivity detector and arranged in a further Wheatstone bridge, the further thermal conductivity detector being configured to operate the further sensing element at a second operating temperature different from the first operating temperature and to detect the separated components and to generate a further detector signal in response to each of the detected components; and
    an evaluation unit for evaluating detector signals and further detector signals to determine a concentrations of the detected components;
    wherein the thermal conductivity detector and the at least one further thermal conductivity detector are calibrated for different concentration ranges; and
    wherein the evaluation unit is further configured to compare the detector signal for currently detected component with the further detector signal to determine in which of the different concentration ranges the concentration of the currently detected component is located and to output a concentration value determined from a signal of the thermal conductivity detector that is calibrated for the concentration of the component detected.

2. The gas chromatograph of claim 1, wherein a thermal conductivity detector having a sensing element with a higher operating temperature is calibrated for components of lower concentrations; and wherein a thermal conductivity detector having a sensing element with a lower operating temperature is calibrated for components of higher concentrations.

3. The gas chromatograph of claim 1, wherein the at least one further detector is identical in configuration to the thermal conductivity detector.

4. The gas chromatograph of claim 2, wherein the at least one further detector is identical in configuration to the thermal conductivity detector.

5. The gas chromatograph of claim 1, wherein the sensing element of the thermal conductivity detector and the further sensing element of the at least one further thermal conductivity detector are thermally coupled on a common substrate.

6. The gas chromatograph of claim 2, wherein the sensing element of the thermal conductivity detector and the further sensing element of the at least one further thermal conductivity detector are thermally coupled on a common substrate.

7. The gas chromatograph of claim 3, wherein the sensing element of the thermal conductivity detector and the further sensing element of the at least one further thermal conductivity detector are thermally coupled on a common substrate.

8. The gas chromatograph of claim 1, wherein the sensing element of the thermal conductivity detector and the further sensing element of the at least one further thermal conductivity detector are integrated in a single component.

9. The gas chromatograph of claim 2, wherein the sensing element of the thermal conductivity detector and the further sensing element of the at least one further thermal conductivity detector are integrated in a single component.

10. The gas chromatograph of claim 3, wherein the sensing element of the thermal conductivity detector and the further sensing element of the at least one further thermal conductivity detector are integrated in a single component.

11. The gas chromatograph of claim 1, wherein the sensing element of the thermal conductivity detector and the further sensing element of the at least one further thermal conductivity detector each have at least one heated filament in a tubular channel.

* * * * *